(12) United States Patent
Köppe

(10) Patent No.: US 12,378,709 B2
(45) Date of Patent: *Aug. 5, 2025

(54) BRAIDED MEDICAL DEVICE AND MANUFACTURING METHOD THEREOF

(71) Applicant: Occlutech GmbH, Jena (DE)

(72) Inventor: Michael Köppe, Jena (DE)

(73) Assignee: Occlutech GmbH, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/500,427

(22) Filed: Nov. 2, 2023

(65) Prior Publication Data

US 2024/0060221 A1 Feb. 22, 2024

Related U.S. Application Data

(60) Continuation of application No. 18/051,716, filed on Nov. 1, 2022, now Pat. No. 11,840,779, which is a (Continued)

(30) Foreign Application Priority Data

May 23, 2010 (EP) ..................................... 10163680

(51) Int. Cl.
*D04C 1/06* (2006.01)
*A61B 17/00* (2006.01)
*A61B 17/12* (2006.01)

(52) U.S. Cl.
CPC ............... *D04C 1/06* (2013.01); *A61B 17/00* (2013.01); *A61B 17/0057* (2013.01); (Continued)

(58) Field of Classification Search
CPC .... D04C 1/06; A61B 17/0057; A61B 17/1214
See application file for complete search history.

(56) References Cited

U.S. PATENT DOCUMENTS

| 5,741,297 A | 4/1998 | Simon |
| 9,271,736 B2 | 3/2016 | Heipl |

(Continued)

FOREIGN PATENT DOCUMENTS

| WO | WO2008/040555 A2 | 4/2008 |
| WO | WO-2024130010 A1 * | 6/2024 |

OTHER PUBLICATIONS

U.S. Appl. No. 11/512,416 B2, filed Nov. 29, 2022, Köppe.
(Continued)

*Primary Examiner* — Tajash D Patel
(74) *Attorney, Agent, or Firm* — Inskeep IP Group, Inc.

(57) ABSTRACT

An medical implantable occlusion device (100) is disclosed having a collapsed state and an expanded state and comprising a braiding (101) of at least one thread, and a distal end (102) comprised of said braiding. The distal end comprises loops (103, 104, 204, 304) formed by loop strands (105, 106, 206, 306) of the at least one thread, wherein, at least in said expanded state, each loop strand has a curved shape and extends away from a centre point (117) of the distal end, whereby an apex point (107, 108, 208, 308) of each of the loop strands corresponds to the turning point of the curved shape and to the point of each of the loop strands being arranged closest to the centre point. At least one of the loop strands is displaced from the centre point by a centre distance (109, 110, 210, 310), and the apex point lie at a distance from a periphery (113) of the distal end.

21 Claims, 10 Drawing Sheets

Related U.S. Application Data continuation of application No. 16/928,848, filed on Jul. 14, 2020, now Pat. No. 11,512,416, which is a continuation of application No. 16/183,622, filed on Nov. 7, 2018, now Pat. No. 10,808,341, which is a continuation of application No. 15/051,027, filed on Feb. 23, 2016, now Pat. No. 10,156,030, which is a division of application No. 13/698,981, filed as application No. PCT/EP2011/058382 on May 23, 2011, now Pat. No. 9,271,736.

(60) Provisional application No. 61/347,466, filed on May 24, 2010.

(52) U.S. Cl.
CPC .. *A61B 17/12109* (2013.01); *A61B 17/12145* (2013.01); *A61B 17/12172* (2013.01); *A61B 2017/00526* (2013.01); *A61B 2017/00575* (2013.01); *A61B 2017/00592* (2013.01); *A61B 2017/0061* (2013.01); *A61B 2017/00867* (2013.01)

(56) References Cited

U.S. PATENT DOCUMENTS

| | | |
|---|---|---|
| 10,156,030 B2 | 12/2018 | Köppe |
| 10,808,341 B2 | 10/2020 | Köppe |
| 11,840,779 B2 * | 12/2023 | Köppe ............... A61B 17/00 |
| 2002/0111647 A1 | 8/2002 | Khairkhahan et al. |
| 2004/0044361 A1 | 3/2004 | Frazier et al. |
| 2005/0228434 A1 | 10/2005 | Amplatz et al. |
| 2005/0283962 A1 | 12/2005 | Boudjemline |
| 2006/0224183 A1 | 10/2006 | Freudenthal |
| 2006/0241690 A1 | 10/2006 | Amplatz et al. |
| 2006/0247680 A1 | 11/2006 | Amplatz et al. |
| 2007/0112380 A1 | 5/2007 | Figulla et al. |
| 2007/0225760 A1 | 9/2007 | Moszner et al. |
| 2007/0265656 A1 | 11/2007 | Amplatz et al. |
| 2008/0262518 A1 | 10/2008 | Freudenthal |
| 2009/0082803 A1 | 3/2009 | Adams et al. |
| 2020/0100795 A1 | 4/2020 | Connor |
| 2023/0381000 A1 * | 11/2023 | Eller ................... D04C 1/02 |
| 2024/0108354 A1 * | 4/2024 | Xu ............... A61B 17/12113 |

OTHER PUBLICATIONS

United States Patent and Trademark Office, Notice of Allowance mailed Oct. 23, 2015 in U.S. Appl. No. 13/698,981, 14 pages.
WIPO, European International Preliminary Examining Authority, International Preliminary Report on Patentability mailed Sep. 27, 2012 in International Patent Application No. PCT/EP2011/058382, 18 pages.
WIPO, European International Search Authority, International Search Report mailed Sep. 20, 2011 in International Patent Application No. PCT/EP2011/058382, 3 pages.

* cited by examiner

Prior art

BRAIDED MEDICAL DEVICE AND MANUFACTURING METHOD THEREOF

RELATED APPLICATIONS

This application is a continuation U.S. patent application Ser. No. 18/051,716 filed Nov. 1, 2022 entitled Braided Medical Device And Manufacturing Method Thereof, which is a continuation of U.S. patent application Ser. No. 16/928,848 filed Jul. 14, 2020 entitled Braided Medical Device And Manufacturing Method Thereof (now U.S. Pat. No. 11,512,416 issued Nov. 29, 2022), which is a continuation of U.S. patent application Ser. No. 16/183,622 filed Nov. 7, 2018 entitled Braided Medical Device And Manufacturing Method Thereof (now U.S. Pat. No. 10,808,341 issued Oct. 20, 2020), which is a continuation of U.S. patent application Ser. No. 15/051,027 filed Feb. 23, 2016 entitled Braided Medical Device And Manufacturing Method Thereof (now U.S. Pat. No. 10,156,030 issued Dec. 18, 2018), which is a divisional of U.S. patent application Ser. No. 13/698,981 filed Jun. 4, 2013 entitled Braided Medical Device And Manufacturing Method Thereof (now U.S. Pat. No. 9,271,736 issued Mar. 1, 2016), which is the U.S. National Phase of and claims priority to International Patent Application No. PCT/EP2011/058382, International Filing Date May 23, 2011, entitled Braided Medical Device And Manufacturing Method Thereof, which claims benefit of and priority to European Application No. 10163680.1, filed May 23, 2010 entitled Braided Medical Device And Manufacturing Method Thereof; and to U.S. Provisional Application Ser. No. 61/347,466, filed May 24, 2010 entitled Braided Medical Device And Manufacturing Method Thereof; all of which are incorporated herein by reference in their entireties.

FIELD OF THE INVENTION

This invention pertains in general to the field of braided medical devices, as well as methods for manufacturing such devices. More particularly the invention relates to braided occlusion devices.

BACKGROUND OF THE INVENTION

Various braided medical devices are used for treating various conditions in a patient. In certain circumstances, it may be necessary to use such devices for occlusion of a patient's lumen, vessel, chamber, channel, hole, or cavity. When delivering or implanting such devices into the patient's body it is critical that the braided device is sufficiently flexible for safe delivery by a delivery device such as a catheter to a target site in the patient. The ease of operation by which the medical device can be delivered is crucial from several aspects such as requirements to comply with time limits for quick treatment or overall safe positioning or maneuvering of the device at the target site.

Issues with some prior art solutions are that the braided devices are not sufficiently flexible, and/or that a large force is required to manipulate the device, for example due to too high stiffness of the braided mesh of the device. This may lead to a difficult delivery of the braided device through for example a catheter. For braided devices having an expanded and a collapsed shape configuration the large force needed to collapse the device from the relaxed expanded state may lead to difficulties to pull the device into for example the delivery sheath of the catheter. Also, due to this force, making these braided device less flexible, the friction between the device and the catheter will be too high in order to easily move and manipulate the device in the catheter, for both movement to pull and to push the device in the catheter. Thus, there is a need for a braided device which allows a secure deployment in the patient.

Insufficient flexibility of some braided devices known in the art may also make the positioning of the device in the patient's body more difficult, for example, by the inability for the device to adapt to the unique anatomy of the target site. Further, a stiff device may lead to injury at the target site, for example to soft tissues in contact with the device. There is accordingly a need for a braided device which adjusts for differences in the anatomies between patients. Further an inflexible device may cause embolies, which could be transported to organs such as the brain and cause blood clots. This appears in particular to be the case with some devices having ends clamped together. In particular it may be an issue to have a distal end having a structure protruding into an arterial (high blood pressure) blood stream leading to vital organs, such as the brain. One issue are protruding threaded clamps keeping together a bundle of strands, such as described in WO99/12478.

WO2008/040555 discloses a braided occlusion device having folded sections in two or more layers for positioning in an opening. Sections at the distal portion of the device are back-bent towards the proximal portion to contact the tissue of the wall having the opening to be occluded. The folded sections cause the device to exhibit a substantial amount of wires to be deformed when compressing the device, hence increasing the force necessary to compress the device and the cross-section of the compressed device.

US2005/0283962 discloses a method of manufacturing a device of a tubular braiding. An issue with tubular braidings as disclosed in US2005/0283962 is insufficient stability that may lead to dislocation of the device from the implanted site.

An issue with prior art braided devices is that catheters with too large cross-section are required, as the devices take up large space even when in the collapsed state. Some regions of the body may thus only be reached with difficulty by such devices requiring large diameter catheters.

A further disadvantage with prior art is that some devices designed to be flexible may not have the sufficient retention force to withstand external forces.

Above disadvantages and issues may have dire consequences for the patient and the health care system. Patient risk may be increased.

Hence, an improved implant would be advantageous and in particular allowing for increased flexibility, cost-effectiveness, and/or patient safety would be advantageous. Also, and a method for manufacturing such medical implant would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a device and a method according to the appended patent claims.

Embodiments of the present invention may be well suited for the selective occlusion of a vessel, lumen, channel, hole, cavity, or the like. Examples, without limitations, are a vessel, lumen, channel, or hole through which blood flows from one vessel to another vessel such as an Atrial Septal Defect (herein after ASD) or a Ventricular Septal Defect (herein after VSD). Other examples could be an Arterial Venous Fistula (AVF), Arterial Venous Malformation (AVM), a Patent Foramen Ovale (PFO), Para-Valvular Leak (PVL), or Patent Ductus Arteriosus.

According to a first aspect of the invention a medical implantable occlusion device is provided having a collapsed state and an expanded state and comprising a braiding of at least one thread, and a distal end comprised of the braiding. The distal end comprises loops formed by loop strands of the at least one thread, wherein, at least in the expanded state, each loop strand has a curved shape and extends away from a centre point of the distal end. An apex point of each of the loop strands corresponds to the turning point of the curved shape and to the point of each of the loop strands being arranged closest to the centre point. At least one of the loop strands is displaced from the centre point by a centre distance such that the location of the apex point is different from the centre point.

According to a second aspect of the invention a method of manufacturing a medical implantable occlusion device of a braiding of at least one thread is provided. The method comprises forming loops by loop strands of the at least one thread by an annular braiding tool having a centre point. Each loop strand has a curved shape and extends away from the centre point of the braiding tool. An apex point of each of the loop strands corresponds to the turning point of the curved shape and to the point of each of the loop strands being arranged closest to the centre point. At least one of the loop strands is displaced from the centre point by a centre distance such that the location of the apex point is different from the centre point.

Further embodiments of the invention are defined in the dependent claims, wherein features for the second and subsequent aspects of the invention are as for the first aspect mutatis mutandis.

Some embodiments of the invention provide for a flexible braided medical device that is easy to manipulate in a delivery device and that adapt to varying anatomical sites in a body of a human or animal.

Some embodiments of the invention also provide for secure attachment of a braided medical device in a patient's vascular system.

Some embodiments of the invention provide for a compact braided medical device with maintained flexibility.

Some embodiments of the invention provide for a braided medical device that can be safely delivered to a treatment site in a patient.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION

Figure 1:
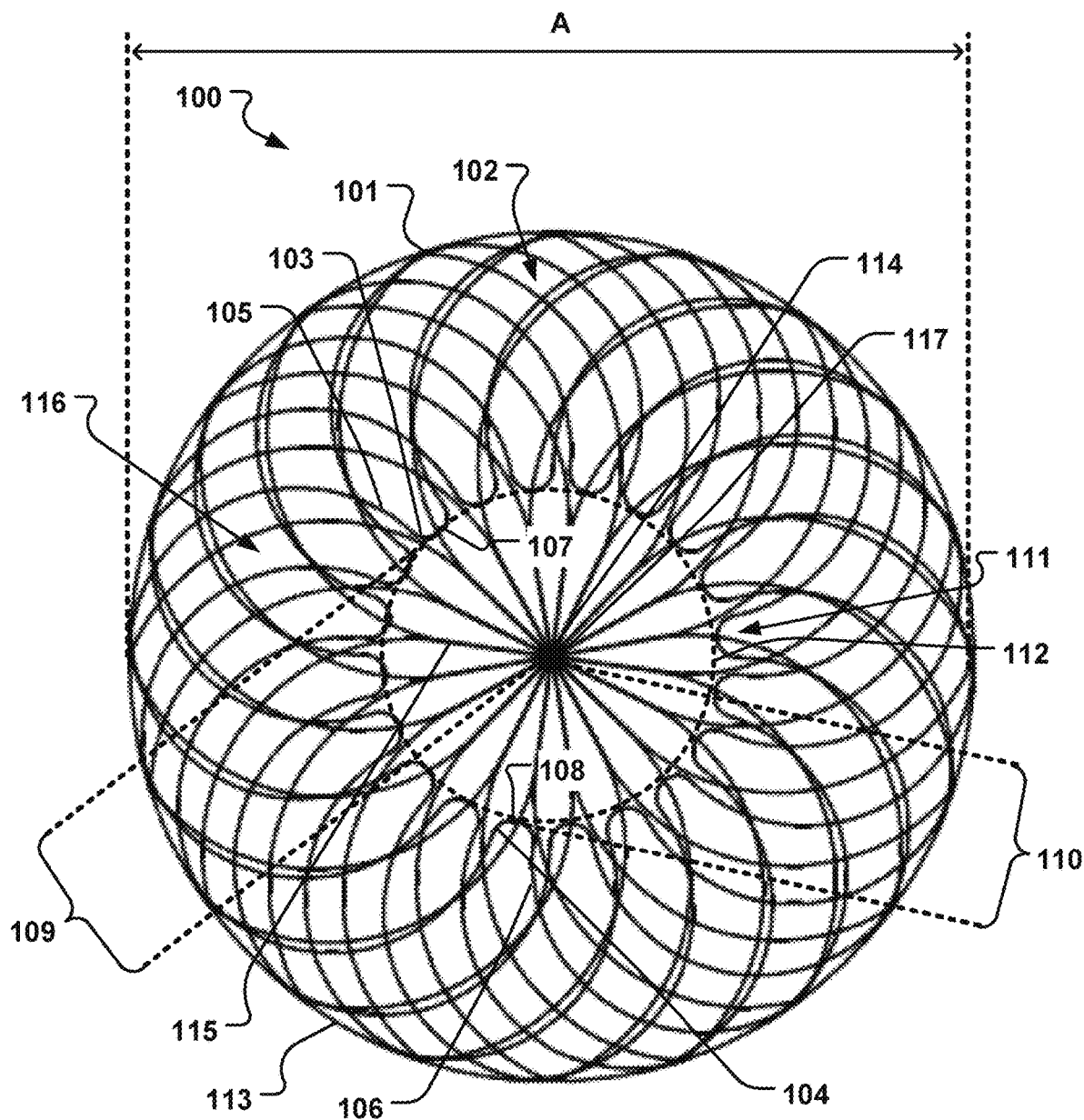
FIG. 1 is an illustration of a braided implantable occlusion device according to an embodiment of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable to PFO or ASD devices. However, it will be appreciated that the invention is not limited to this application but may be applied to many other medical implantable devices, including for example filters, stents, vascular occluders, Left Atrial Appendage (LAA) occluders, aneurysm treatment devices, grafts, etc.

FIG. 1 shows a braided implantable occlusion device 100 according to an embodiment of the invention. The device 100 comprises a mesh or braiding 101 of at least one thread. The braiding 101 may be formed from one thread or several. The device 100, or more particularly the braiding 101, has a collapsed state and an expanded state. FIG. 1 depicts an end of the device 100, which in this case is a distal end 102. In other embodiments (not shown) a proximal end of the device 100, or any other part of the device 100, may have the same features as the distal end 102. Hence any part of the braiding 101 forming the device may have the features described in the following, with the associated advantages. The distal end 102 is comprised of the braiding 101.

The braiding 101 may be made of a material suitable for implanting in a human or animal body, and suitable for being formed in a heat treatment procedure to a desired shape in an expanded state and also in the collapsed state. For example NiTinol may be used as a material for the device 100. However, suitable materials for embodiments of the braiding are various and include shape memory materials, metal, superelastic alloys (such as NiTinol), or polymers, such as degradable polymers.

The distal end 102 comprises loops 103, 104, formed by loop strands 105, 106, of the at least one thread. In at least the expanded state each loop strand 103, 104, has a curved shape and extends away from a centre point 117 of the distal end 102. Thus, each of the loop strands 105, 106 has an apex point 107, 108, corresponding to the turning point of the curved shape and to the point of each of the loop strands that are closest to the centre point 117.

In FIG. 1 the loops 103, 104, are U-shaped but may have other shapes of the open curvature, e.g. elliptical, half circular, or W-shaped. The curved shape of the loop strands 103, 104 extending away from the centre point 117 should be construed as the opening of the U-shaped curve points radially outwards from the centre point 117.

At least one of the loop strands 105, 106, is displaced from the centre point 117 by a centre distance 109, 110, such that the location of the apex point 107, 108 is different from the centre point 117.

The centre distance 109, 110, between the apex 107, 108, and the centre point may vary, and is preferably less than half the diameter (A) of the device 100, or less than half the cross-section at the location of the apex point in case the device 100 is non-circular.

By having a displacement of at least one of the loop strands 105, 106, from the centre point 117 the device 100 may exhibit a smaller cross-section or diameter in the collapsed state of the device 100, as less strands are present at the tip or centre point 117 of the device. At the same time by having the apex point 107, 108, at a distance from the periphery 113 of the distal end 102 stability of the device 100 is maintained. I.e. a partly closed distal end 102 is obtained even if no centre strands 115 extend across the centre point 117, as shown in FIG. 4. Having a partly closed distal end 102, i.e. where the apex points 107, 108, of the loop strands are positioned between the centre 105 and the periphery 113 of the distal end 102, may also facilitate occlusion by allowing for easier fixing of a membrane (not shown) in the braiding 101 of the distal end 102 due to a part of the braiding 101 of the distal portion 102 extending in the radial direction. The braiding 101 extending in the radial direction at the distal end 102 may also improve the occlusion ability itself without the need for additional elements. As shown in FIGS. 2-6, 8, the apex points 107, 108, may be displaced from the centre 105 by different distances. The flexibility of the device 101 may thereby be improved while maintaining structural rigidity.

Figure 8:
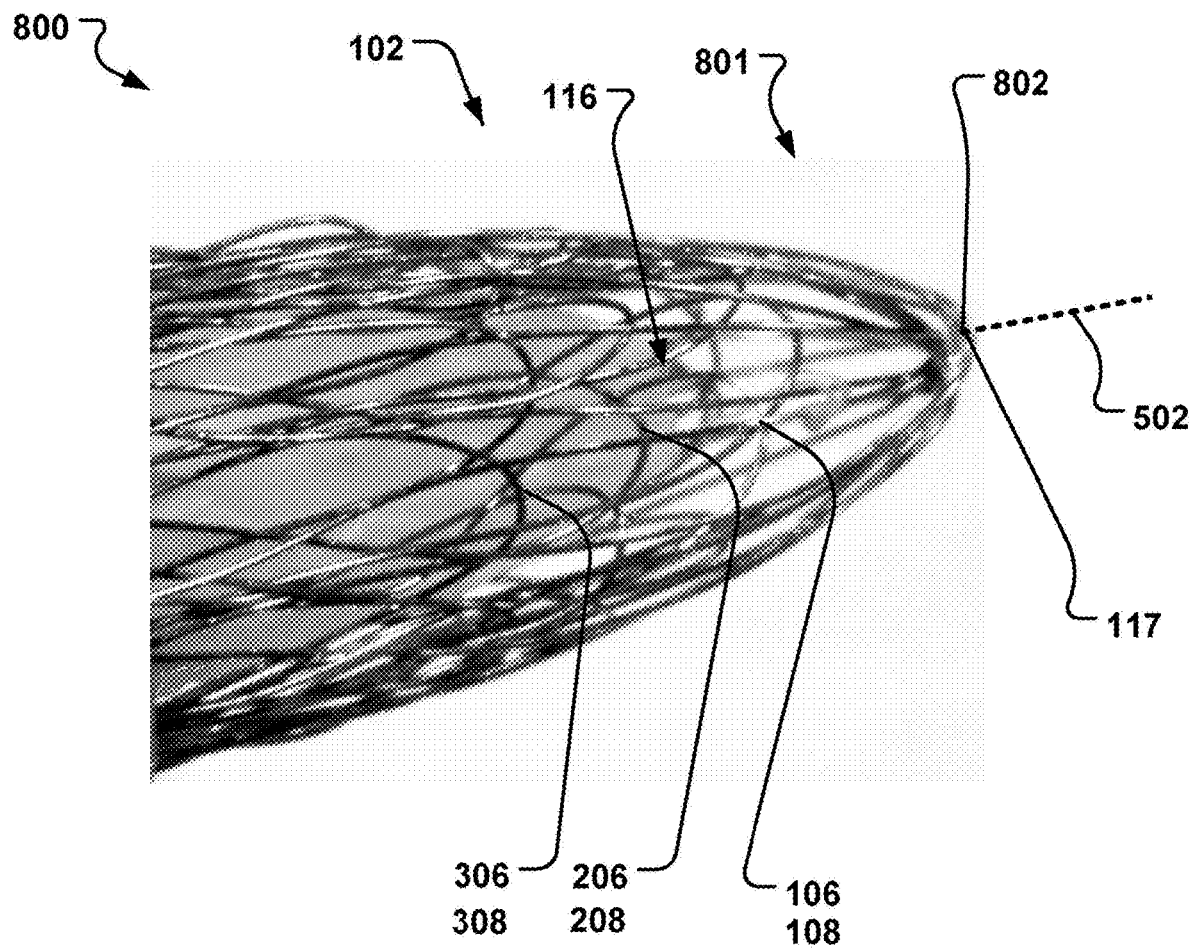
FIG. 8 shows the braided implantable occlusion device according to an embodiment of the invention.

If the device 100 is stretched substantially along a longitudinal axis 502 passing through the centre point 117, see FIG. 8, the centre point 117 will correspond substantially to the tip of the device 100.

The device 100, 200, 300, 400, 500, 600, is preferably collapsed by stretching. The device 100, 200, 300, 400, 500, 600, may also be collapsed by compression. Hence, as the loop strands 105, 106, and further loop strands 206, 306, according to embodiments in FIG. 3, and FIG. 8, are displaced from the centre point 117 less strands will be present at the tip 801 which may reduce the cross-section of the tip 801.

The apex point 107, 108, 208, 308, of each of the loop strands may be displaced from the centre point 117 along a longitudinal axis 502 when the device is in the collapsed state. The centre point 117 may correspond to a distal tip 802 when the device 100, 200, 300, 400, 500, 600, is in the collapsed state, as shown in FIG. 8.

The braiding of the distal end 102 may comprise a distal surface 116 of the at least one thread. The distal surface 116 extends from the apex point 107, 108, 208, 308, of each of said loop strands to the centre point 117. The distal surface 116 may comprise the loop strands 105, 106, 206, 306, or centre strands 115. In case the device 100, 200, 300, 400, 500, 600, is in the collapsed state the distal surface 116 may extend from the apex point 107, 108, 208, 308, of each of said loop strands to the distal tip 802 of the device, as shown in FIG. 8. Hence, the braiding 101 in which the apex points 107, 108, 208, 308, is confined, may be continuous from these apex points to the centre point 117. As shown in FIG. 4 the distal end 102 of the device 400 may also be open. The centre strands 115 improves the stability of the device, and/or occlusion effectiveness, while the flexibility and small cross-section is maintained in the collapsed state due to the loop strands being displaced from the centre point 117.

Figure 3:
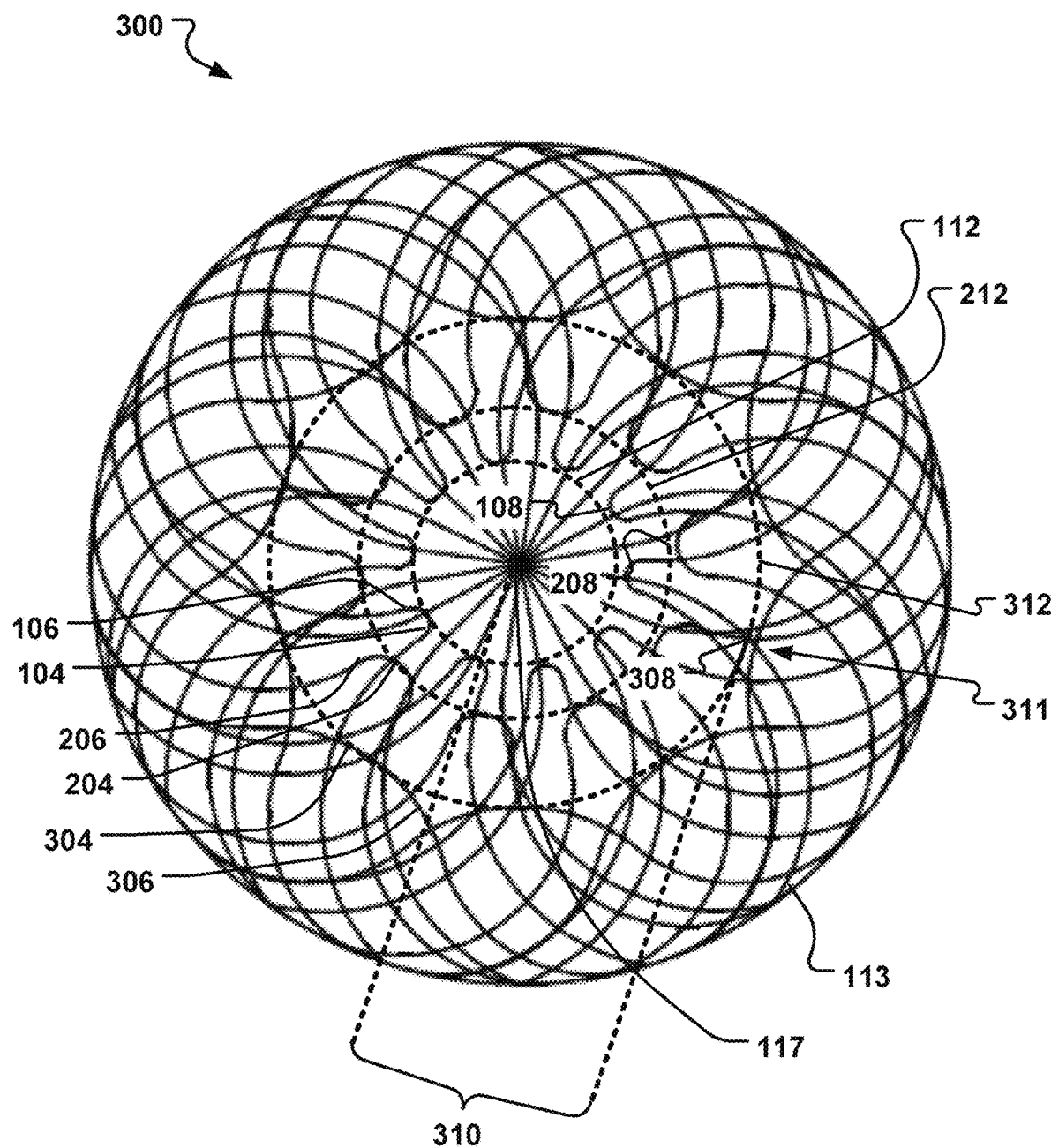
FIG. 3 is an illustration of a braided implantable occlusion device according to another embodiment of the invention.
Figure 4:
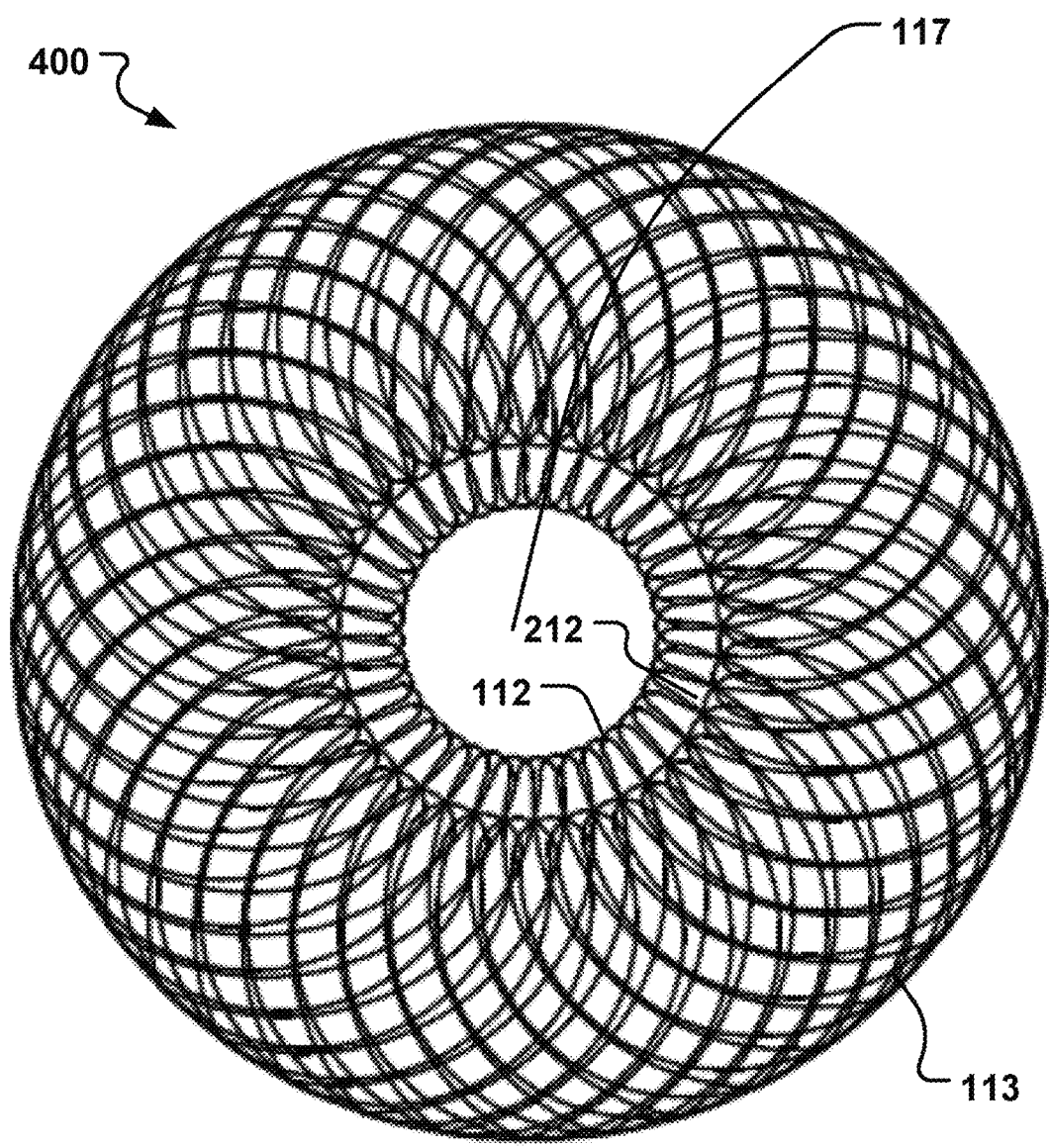
FIG. 4 is an illustration of a braided implantable occlusion device according to another embodiment of the invention.

By having a plurality of loop strands displaced from the centre point 117 by a plurality of centre distances 109, 110, and further displacement by centre distances 206, 306, according to embodiments in FIG. 3, and FIG. 8, a larger portion of the distal end 102 may exhibit a smaller cross-section in the collapsed state of the device 100. Further, the cross-section of the entire device 100 may be reduced by the displacement. FIG. 8 may be illustrative of a device 100 in both the collapsed state and in the expanded state. Hence, the cross-section may be reduced in the expanded state as well. By provision of a smaller cross-section the device 100 in the collapsed state the device 100 may be delivered to a target site in a patient through a delivery device with a reduced cross-section, which may lead to an easier delivery procedure or manipulation of the delivery device in the patient.

Further thanks to the displacement of the loop strands 105, 106, 206, 306, from the centre point 117 the amount of force required to compress the device from the expanded state, as illustrated in FIG. 1-4, to the collapsed state, as illustrated in FIG. 8, is reduced. This is thanks to the fact that the loop strands 105, 106, 206, 306, do not cross the centre point 117. Thus, the amount of threads that must be bent at the centre point 117 when compressing the device 100 is reduced. Each thread crossing the centre point 117 or a region close to the centre point 117 that is subjected to substantial deformation when compressing the device 100 to the collapsed state has a certain amount of structural integrity and an associated force that must be exceeded in order to deform the thread. By having several loop strands 105, 106, 206, 306 displaced from the region subjected to the most of the deformation, e.g. the centre point 117 or tip 801, the force required for deformation is thus substantially reduced. A more flexible braided device 100-600 is thus obtained, which for example can be more easily retracted into a catheter sheath and which exerts less frictional force on the walls of the catheter thereby increasing the ease of operation of the device 100-600 in the catheter, for example during push and pull motion.

In FIG. 1 the device 100 comprises a group 111 of a plurality of loop strands 105, 106, that are displaced from the centre point 117 such that the apex points 107, 108, of the group 111 lie on an imaginary circle 112 enclosing the centre point 117. The apex points 107, 108 also lie at a distance from a periphery 113 of the distal end 102.

Figure 2:
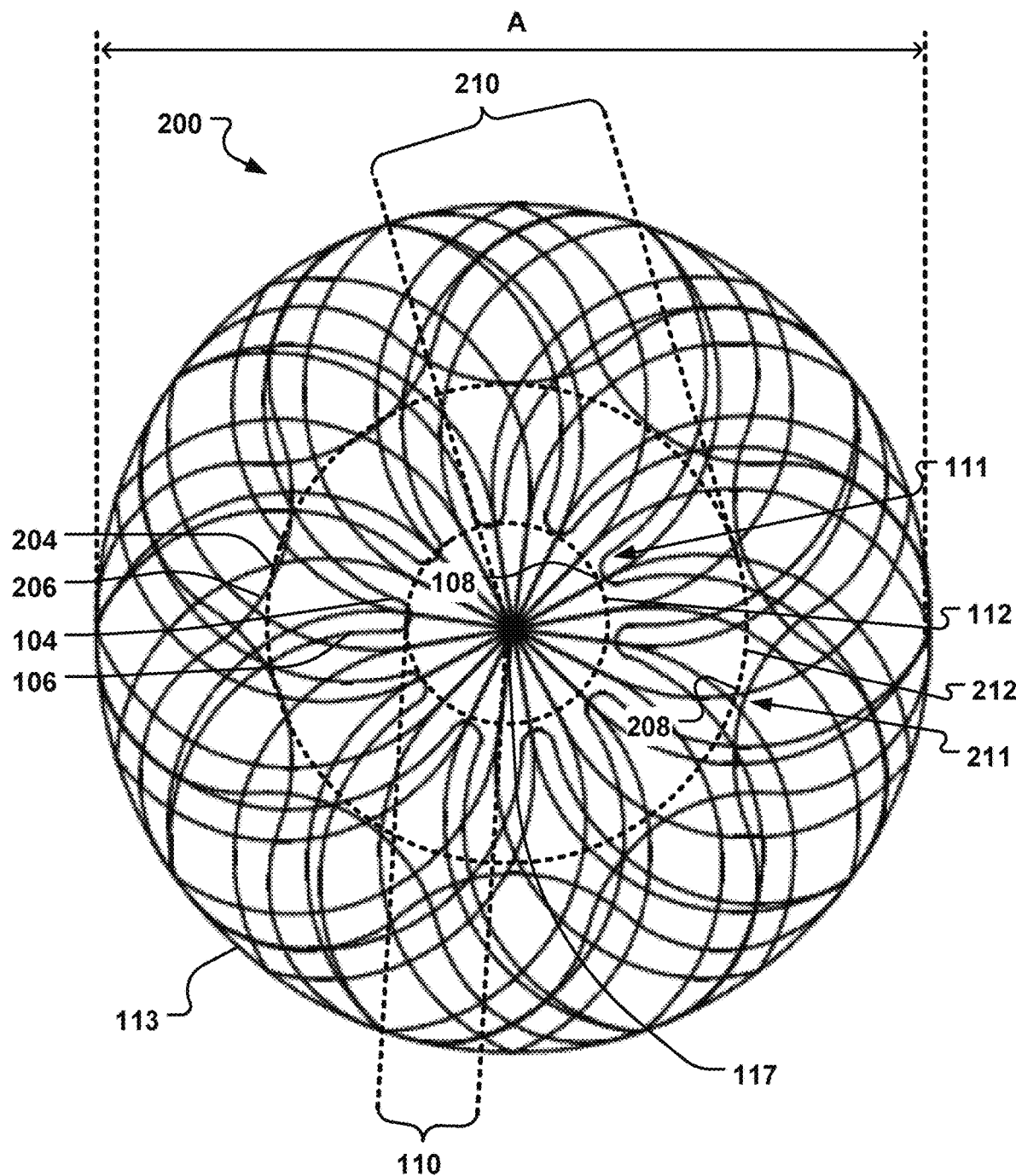
FIG. 2 is an illustration of a braided implantable occlusion device according to another embodiment of the invention.

The stability of the device is thereby improved as compared to the case when the wires turn at the periphery of the braiding, as with the distal end of a device of a tubular braiding. It is also easier to manufacture the device according to the invention compared to such tubular braidings. As illustrated in FIGS. 1-4 the distance the apex points lies from the periphery 113 may vary from less than half of the radius, e.g. at a fourth of the radius, to more than half the radius, e.g. three fourths of the radius. Similarly, FIG. 2-4 shown devices 200-400 comprising at least one group 111, 211, 311 of a plurality of loop strands 105, 106, 206, 306, that are displaced from the centre point 117 such that the apex points 107, 108, 208, 308, of the at least one group lie on at least one imaginary circle 112, 212, 312 enclosing the centre point 117. The apex points 107, 108, 208, 308, also lie at a distance from a periphery 113 of the distal end 102. The radius of the at least one imaginary circle 112, 212, 312 corresponds to the centre distances 109, 110, 210, 310. An increased radius may provide a more flexible device 100-400 with less force required for compression of the device 100-400 from its expanded state to its collapsed state.

The at least one imaginary circle 112, 212, 312 may have its circle centre 114 corresponding to the location of the centre point 117. Thereby, the at least one group 111, 211, 311 of the plurality of loop strands 105, 106, 206, 306, are displaced concentrically from the centre point 117. Alternatively, the device 100-400 may have an asymmetrical position of the at least one imaginary circle 112, 212, 312 with respect to the centre point 117. Optionally, imaginary circles 112, 212, 312 may be equidistantly distributed from each other in radial direction of the distal end 102.

In FIG. 2 the loop strands 106, 206, comprise two groups 111, 211, of pluralities of loop strands. The first group 111 and the second group 211 of the plurality of loop strands have a first and second plurality of apex points 108, 208, respectively. The first and second plurality of loop strands are displaced from the centre point 117 such that the first plurality of apex points 108 lies on the periphery of an imaginary circle 112 having a first radius 110 and the second plurality of apex points 208 lies on the periphery of an imaginary circle 212 having a second radius 210 which different from the first radius 110. The first and second radius 110, 210, are less than the diameter (A) of the distal end 102.

In FIG. 3 a third group 311 of the plurality of loop strands has a third plurality of apex points 308 that lies on the periphery of an imaginary circle 312 having a third radius 310 different from the first and second radius 110, 210.

The first, second, and third groups 111, 211, 311, of the plurality of apex points 108, 208, 308, may lie concentrically with respect to the centre point 117.

Each group 111, 211, 311, of the pluralities of loop strands may be formed by a plurality of threads respectively, or by a single thread. The braiding may 101 comprise any number of threads.

The distal end 102 may be closed, as shown in FIG. 1-3, preferably by a plurality of centre stands 115 of the braiding 102 crossing each other at the centre point 117. The distal end 102 may also be open, as shown in FIG. 4. An open distal end 102 may be advantageous in some applications.

The amount of the centre strands 115 may be varied. The flexibility of the device 100-600 may be adjusted by varying the amount of centre strands 115, hence providing customization of the device 100-600 to various applications. Fewer centre strands 115 may decrease the force required for compressing the device 100-600 from the expanded state to the collapsed state, hence increasing the flexibility. The ratio between the amount of the centre strands 115 and the loop strands may be set to a defined value. In FIG. 1 and FIG. 2 50% of the threads are looped back, i.e. are comprised of loop strands 105, 106, 206, 306. In FIG. 2 75% of the threads are looped back, and in FIG. 4 100% of the threads are looped back. By varying the amount of loop strands the flow through the device may also be optimized. More or less dense loop strands or more strands crossing the centre may increase the maximum flow throughput of the device.

The device may comprise biocompatible fibres or patches of for example of PET that support sealing of the blood flow through the device.

Each of the apex points 107, 108, 208, 308 may be equally spaced apart around the peripheries of the at least one imaginary circle 112, 212, 312.

The distal end 102 may have any shape such as a circular disc shape, and/or spherical shape, and/or elongate shape.

Figure 5A:
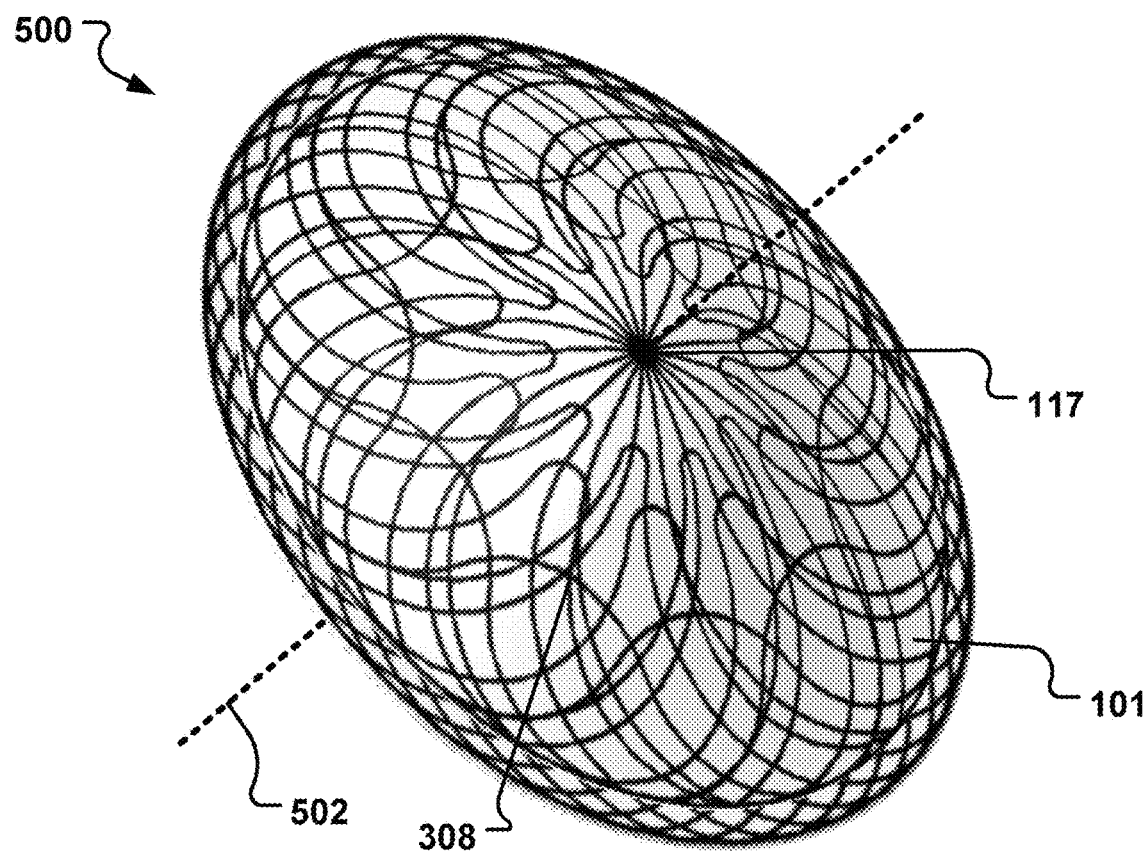
FIGS. 5a-b are illustrations of a braided implantable occlusion device according to another embodiment of the invention.
Figure 5B:
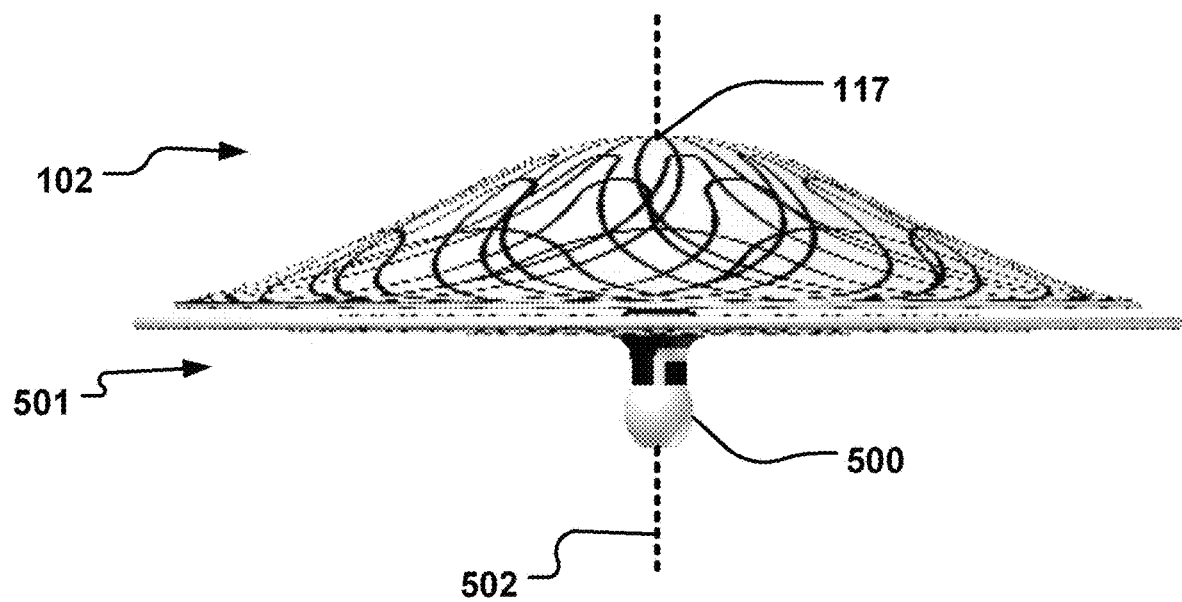

FIG. 5a shows a perspective view of a device 500 having a braiding 101 according to the embodiment in FIG. 3. FIG. 5b show a side view of the device 500 in FIG. 5a according to an embodiment. FIGS. 5a-b may represent a PFO occluder with two double layer discs. The braiding 101 of the device 500 may comprise loop strands according to any of the devices 100-400, e.g. one, two, or more groups of loop strands being displaced from the centre point 117 at different distances.

As shown in FIGS. 5a-b, a longitudinal axis 502 extends between centre points of the distal and proximal ends the device 500. The occlusion device 500 has rotational symmetry around the longitudinal axis 502, and the centre point 117 coincide with the intersection of the longitudinal axis 502 with the distal end 102 of the device 500, which may also be the case for the devices 100-400.

Figure 6A:
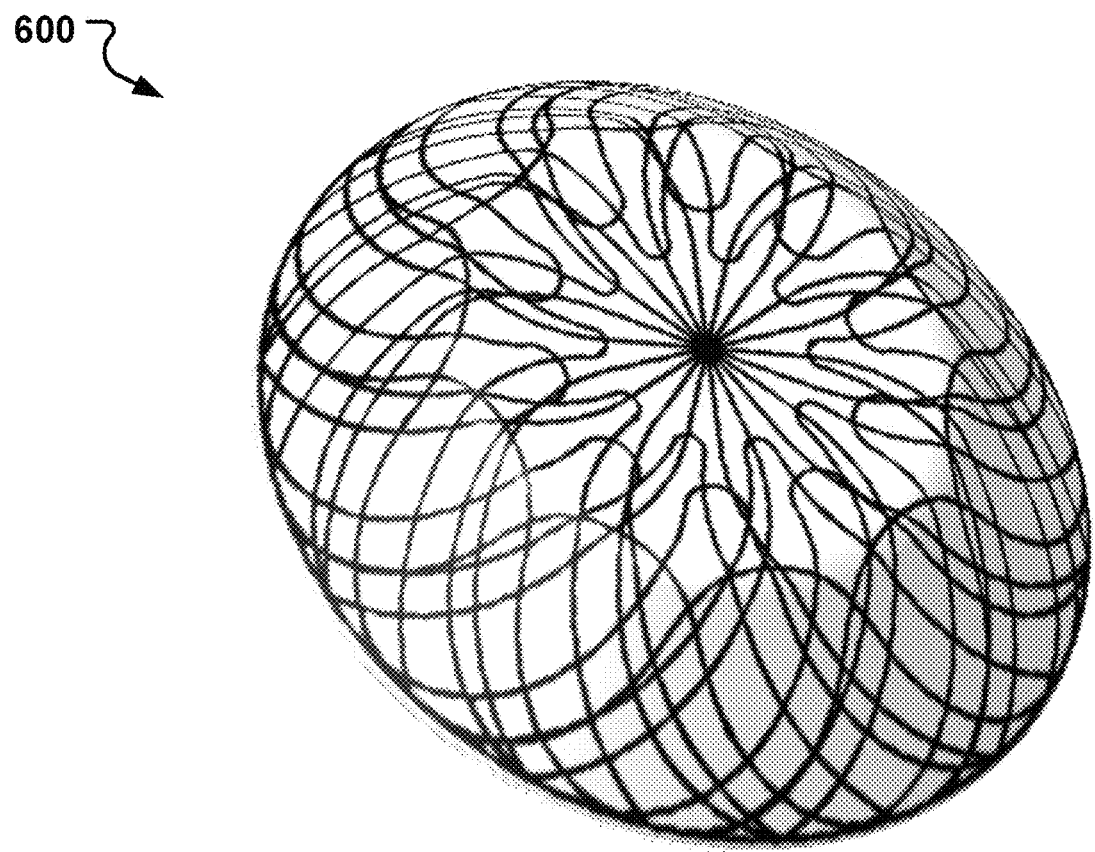
FIGS. 6a-b are illustrations of a braided implantable occlusion device according to another embodiment of the invention.
Figure 6B:
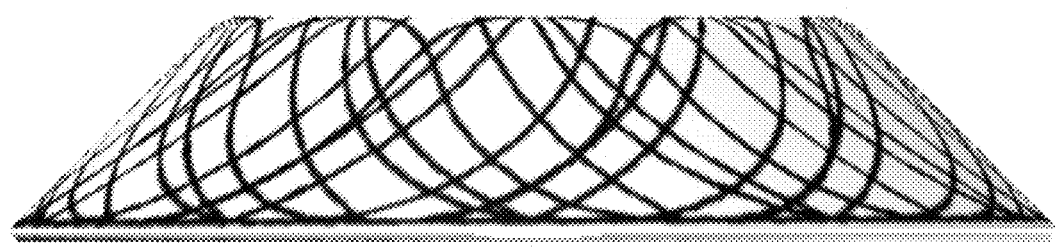

FIG. 6a shows a perspective view of a device 600 having a braiding 101 according to the embodiment in FIG. 3. FIG. 6b show a side view of the device 600 in FIG. 6a according to an embodiment. FIGS. 6a-b may represent an ASD occluder with two double layer discs. The braiding 101 of the device 600 may comprise loop strands according to any of the devices 100-400.

Figure 7A:
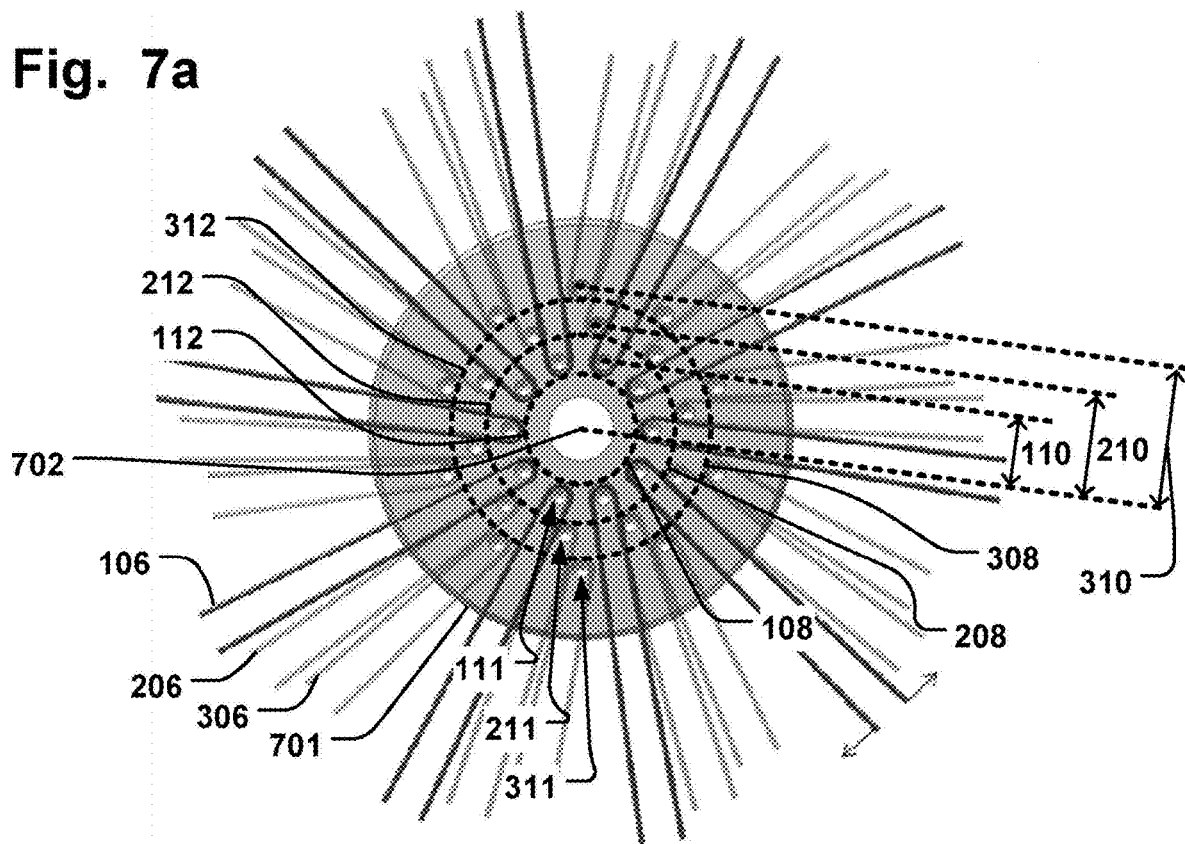
FIGS. 7a-b are illustrations of a method for manufacturing of a braided implantable occlusion device according to an embodiment of the invention.
Figure 7B:
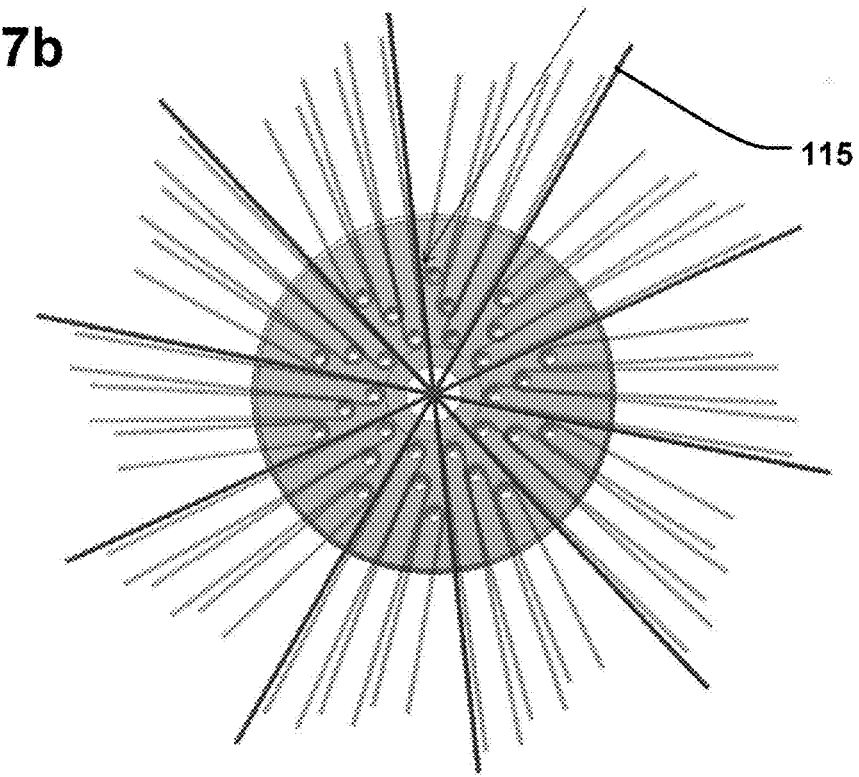
Figure 9:
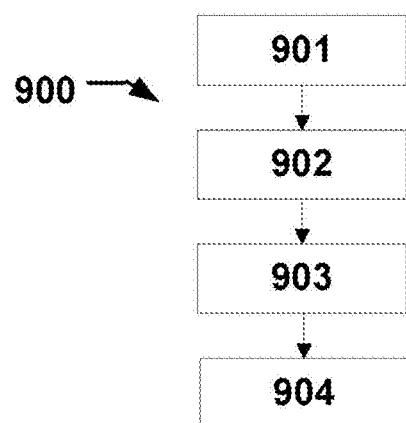
FIG. 9 shows a method of manufacturing a medical implantable occlusion device according to an embodiment of the invention.
Figure 10A:
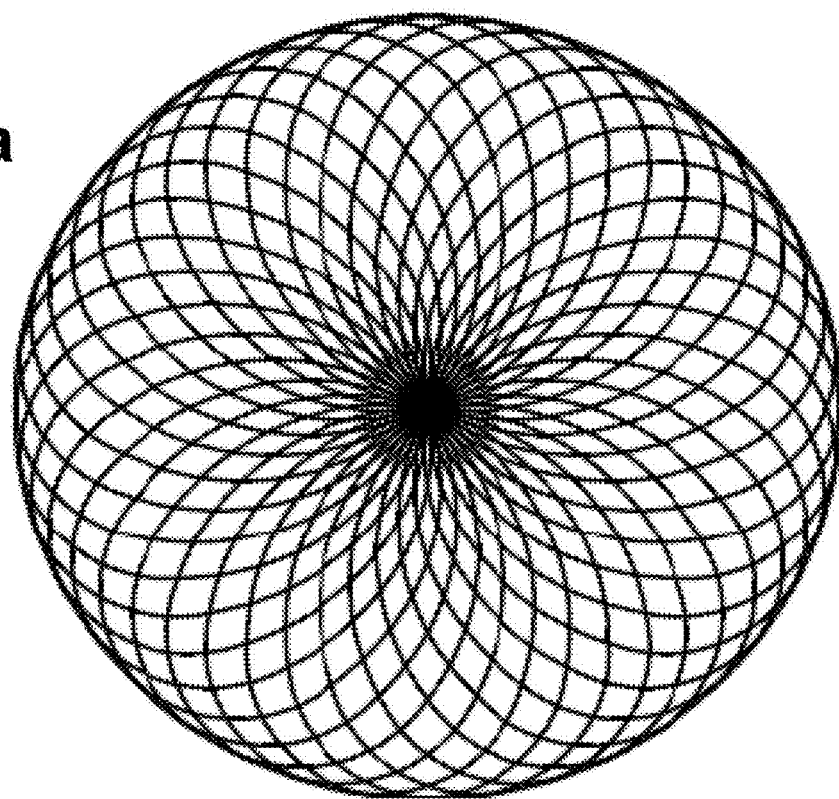
FIGS. 10a-b are illustrations of prior art devices.
Figure 10B:
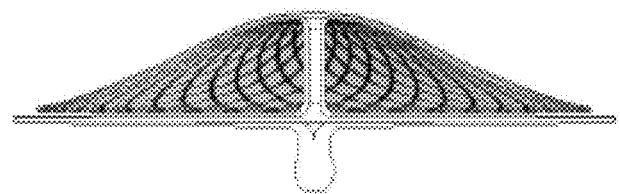

FIGS. 7a-b and FIG. 9 illustrates a method 900 of manufacturing a medical implantable occlusion device 100-400 of a braiding 101 of at least one thread. The method 900 comprises forming 901 loops by loop strands 106, 206, 306 of the at least one thread by an annular braiding tool 701 having a centre point 702. Each loop strand 106, 206, 306 has a curved shape and extends away from the centre point 702 of the braiding tool 701. The apex point 108, 208, 308, of each of the loop strands 106, 206, 306, corresponds to the turning point of the curved shape and to the point of each of the loop strands 106, 206, 306, being arranged closest to said centre point 702. At least one of the loop strands 106, 206, 306, is displaced from the centre point 702 by a centre distance 110, 210, 310, such that the location of the apex point 108, 208, 308, is different from the centre point 702. As is shown in FIG. 7a-b the apex points 108, 208, 308, lie at a distance from the peripheral edge of the braiding tool 701. A partially closed braiding 101, as discussed above, with returning loops may thereby be manufactured with improved stability over a mere tubular braiding, while maintaining flexibility. An improved occlusion ability is also provided, e.g. by the braiding 101 extending in the radial direction of the distal end 102, or by easier incorporation of a membrane (not shown) in the braiding. As shown in FIG. 7a-b the apex points 108, 208, 308, lie at different distances from the periphery of the braiding tool 701 or from the centre point 702. A braiding 101 with the loop strands displaced from the centre 105 of the braiding 101 by different distances may thereby be manufactured. A device 100, 200, 300, 400, 500, 600, having such braiding 101 has the advantages as described above.

The method 900 comprises forming 902 at least one group 111, 211, 311, of a plurality of loop strands being displaced from the centre point 702 such that the apex points 108, 208, 308, of the at least one group lie on at least one imaginary circle 112, 212, 312, enclosing the centre point 702.

The loops may be formed without crossing the loop strands 106, 206, 306, with each other.

The method 900 may comprise forming 903 a closed end of the braiding by crossing 904 the centre point 702 with a plurality of centre strands 115.

The present invention has been described above with reference to specific embodiments. However, other embodiments than the above described are equally possible within the scope of the invention as defined by the appended patent claims. The different features and steps of the invention may be combined in other combinations than those described. The scope of the invention is only limited by the appended patent claims.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

What is claimed is:

1. A method of selectively occluding a vessel, lumen, channel or hole through which blood flows from one vessel to another vessel, the method comprising
   a. delivering, in a collapsed state, a medical implantable occlusion device into the vessel, lumen, channel or hole, and
   b. expanding the implantable occlusion device to an expanded state, thereby occluding the vessel, lumen, channel or hole,
   wherein the medical implantable occlusion device comprising:
      a braiding of at least one thread forming a first end and a second end; and
      in an expanded state, the first end comprising 1) a first periphery and a first center, and 2) thread segments of the at least one thread having a curved shape with an apex located between the first periphery of the first end and the first center of the first end so as to form a plurality of first loops.

2. The method of claim 1, wherein the vessel, lumen, channel or hole through which blood flows from one vessel to another vessel is an Atrial Septal Defect (ASD) or a Ventricular Septal Defect (VSD).

3. The method of claim 1, wherein an opening through the first end and the second end extends along a center axis between a proximal end and a distal end of the medical implantable occlusion device.

4. The method of claim 1, wherein in the expanded state, the first end has a circular disc shape, a spherical shape, or an elongated state.

5. The method of claim 1, wherein the thread segments, in the expanded state, cross each other.

6. The method of claim 1, wherein the first end comprises at least two groups of thread segments,
   wherein apices of a first group of thread segments are located about a first radius from the center, and
   wherein apices of a second group of thread segments are located about a second radius from the center.

7. The method of claim 1, wherein the medical implantable occlusion device further comprises at least one center thread segment, wherein the at least one center thread segment crosses the first end near but not across the first center of the first end.

8. The method of claim 1, wherein the occlusion device further comprises an opening through at least the first end.

9. The method of claim 1, wherein in the expanded state, the second end comprises 1) a second periphery and a second center, and 2) thread segments of the at least one thread having a curved shape with an apex located between the second periphery of the second end and the second center of the second end so as to form a plurality of second loops.

10. The method of claim 9, wherein in the expanded state, the second end has a circular disc shape, a spherical shape, or an elongated state.

11. The method of claim 9, wherein the first end is a distal end and the second end is a proximal end.

12. The method of claim 9, wherein the second end comprises at least two groups of thread segments;
   wherein apices of some of the thread segments are located about a first radius from the second center; and
   wherein apices of some of the thread segments are located about a second radius from the second center.

13. The method of claim 9, wherein the plurality of first loops are U-shapes, elliptical, half circle, or W shaped.

14. A method of selectively occluding a vessel, lumen, channel or hole through which blood flows from one vessel to another vessel, the method comprising:
   a. delivering, in a collapsed state, a medical implantable occlusion device into the vessel, lumen, channel or hole, and
   b. expanding the implantable occlusion device to an expanded state, thereby occluding the vessel, lumen, channel or hole,
   wherein the medical implantable occlusion device comprises:
   at least one thread braided to form a first end and a second end;
   in an expanded state, the first end comprising 1) a first periphery and a first center, and 2) thread segments of the at least one thread having a curved shape with an apex located between the first periphery of the first end and the first center of the first end so as to form a plurality of first loops; and
   in the expanded state, the second end comprises 1) a second periphery and a second center, and 2) thread segments of the at least one thread having a curved shape with an apex located between the second periphery of the second end and the second center of the second end so as to form a plurality of second loops.

15. The method according to claim 14, further comprising providing an opening through the first end or the second end.

16. The method according to claim 14, further comprising providing an opening through the first end only.

17. The method of claim 14, wherein the vessel, lumen, channel or hole through which blood flows from one the vessel to the another vessel is an Atrial Septal Defect (ASD) or a Ventricular Septal Defect (VSD).

18. The method of claim 14, wherein the occlusion device further comprises an opening through at least the first end.

19. A method of selectively occluding a vessel, lumen, channel or hole through which blood flows from one vessel to another vessel, the method comprising:
   a. delivering, in a collapsed state, a medical implantable occlusion device into the vessel, lumen, channel or hole, and
   b. expanding the implantable occlusion device to an expanded state, thereby occluding the vessel, lumen, channel or hole,
   wherein the medical implantable occlusion device comprising:

a braided structure formed from at least one thread; and the braided structure comprising a first end means for forming a first periphery means and a first center means; and thread segments of the at least one thread having a curved shape with an apex located between the first periphery means of the first end means and the first center means of the first end means so as to form a plurality of first loops.

20. The method of claim 19, wherein the vessel, lumen, channel or hole through which blood flows from one vessel to another vessel is an Atrial Septal Defect (ASD) or a Ventricular Septal Defect (VSD).

21. The method of claim 19, wherein the occlusion device further comprising an opening through at least the first end means.

\* \* \* \* \*